United States Patent
Morris et al.

(10) Patent No.: US 7,519,413 B1
(45) Date of Patent: Apr. 14, 2009

(54) APPARATUS AND METHOD FOR MEASURING MOTION IN A STRONG MAGNETIC FIELD

(75) Inventors: G. Ronald Morris, Belle Terre, NY (US); Janan A. Hiz, Nesconset, NY (US); Douglas F. Tomlinson, Waunakee, WI (US)

(73) Assignee: S.A. Instruments, Inc., Stony Brook, NY (US)

( * ) Notice: Subject to any disclaimer, the term of this patent is extended or adjusted under 35 U.S.C. 154(b) by 683 days.

(21) Appl. No.: 10/798,100

(22) Filed: Mar. 11, 2004

Related U.S. Application Data

(63) Continuation of application No. 10/371,901, filed on Feb. 20, 2003, now abandoned.

(51) Int. Cl.
  *A61B 5/05* (2006.01)
  *A61B 5/04* (2006.01)
(52) U.S. Cl. .................. 600/411; 600/509; 600/413
(58) Field of Classification Search ............... 600/411, 600/412, 509, 549, 382, 513; 128/901; 324/307, 324/309
See application file for complete search history.

(56) References Cited

U.S. PATENT DOCUMENTS

| | | | |
|---|---|---|---|
| 4,694,837 A | 9/1987 | Blakeley et al. | |
| 4,715,383 A | 12/1987 | Ehman et al. | |
| 4,716,368 A | 12/1987 | Haacke | |
| 4,724,386 A | 2/1988 | Haacke et al. | |
| 4,727,882 A | 3/1988 | Schneider et al. | |
| 4,991,587 A | 2/1991 | Blakeley et al. | |
| 5,035,244 A | 7/1991 | Stokar | |
| 5,038,785 A | 8/1991 | Blakely et al. | |
| 5,139,108 A * | 8/1992 | Pate | 182/129 |
| 5,209,233 A | 5/1993 | Holland et al. | |
| 5,242,455 A | 9/1993 | Skeens et al. | |
| 5,327,888 A * | 7/1994 | Imran | 600/393 |
| 5,427,101 A | 6/1995 | Sachs et al. | |
| 5,464,410 A | 11/1995 | Skeens et al. | |
| 5,482,042 A | 1/1996 | Fujita | |
| 5,657,757 A | 8/1997 | Hurd et al. | |
| 5,671,739 A | 9/1997 | Darrow et al. | |
| 5,729,140 A | 3/1998 | Kruger et al. | |
| 5,879,308 A * | 3/1999 | Rasanen | 600/536 |
| 6,073,041 A | 6/2000 | Hu et al. | |
| 6,088,611 A | 7/2000 | Lauterbur et al. | |
| 6,148,229 A * | 11/2000 | Morris et al. | 600/509 |

(Continued)

*Primary Examiner*—Eric F Winakur
*Assistant Examiner*—Michael T Rozanski
(74) *Attorney, Agent, or Firm*—Amster, Rothstein & Ebenstein LLP

(57) ABSTRACT

The present invention is an apparatus for measuring motion of a portion of the body of a patient and, optionally, electrocardiogram, of a patient in a magnetic field. A pickup coil in the form of a loop positioned around the portion of interest of the body of the patient is formed either by a wire connected to a voltage measuring device or an ECG lead having one end connected to the voltage measuring device and the other end connected to an electrode on the patient. A cradle may be positioned between the loop and the patient to facilitate pickup of the movement of the patient. When the ECG lead is used, a second ECG lead is connected between the voltage measuring device and a second electrode on the patient. The output of the voltage measuring device represents the respiration of the patient, and the electrocardiogram when ECG leads are used.

12 Claims, 4 Drawing Sheets

U.S. PATENT DOCUMENTS 6,161,032 A 12/2000 Acker
6,185,446 B1 2/2001 Carlsen, Jr.
6,945,941 B2 * 9/2005 Eriksen et al. .............. 600/534
2002/0077560 A1 6/2002 Kramer et al.
2002/0120190 A1 8/2002 Chang
2002/0183611 A1 12/2002 Fishbein et al.

* cited by examiner

APPARATUS AND METHOD FOR MEASURING MOTION IN A STRONG MAGNETIC FIELD

CROSS-REFERENCE TO RELATED APPLICATION

This application is a continuation of U.S. patent application Ser. No. 10/371,901, filed Feb. 20, 2003 now abandoned.

FIELD OF THE INVENTION

The invention relates generally to an apparatus and method that detects motion in the presence of a strong magnetic field. More specifically, the invention relates to an apparatus and method which, when coupled to a subject in a magnetic resonance imaging ("MRI") scanner, detects motion, e.g., respiratory activity, through a pickup coil but does not create artifacts in the MRI image.

BACKGROUND OF THE INVENTION

Respiratory motion can cause severe blurring in magnetic resonance imaging ("MRI") studies of the thoracic or abdominal region of a subject (i.e., a person or other animal undergoing medical or scientific treatment or examination) when the total duration of the experiment is not short compared to the respiratory period. For such experiments, a variety of methods exist to reduce the effects of respiratory motion on the resulting images. Such methods can be broadly classified into four different types, modifying the subject of the image, nuclear magnetic resonance ("NMR") based methods, direct non-NMR based methods, and indirect non-NMR based methods.

One method of minimizing motion that causes blurring is to modify the subject in one way or another. For example, the subject can be asked to hold their breath. Although this can minimize respiratory motion and eliminate blurring, it is not applicable to animal subjects and cannot be used with some subjects with respiratory or other illnesses. Subjects can also be intubated, or mechanically ventilated. This permits exact synchronization of MRI data acquisition to the respiratory cycle. However, this may induce significant reductions in cardiac output and liver blood flow compared to free breathing, and is an invasive procedure that is often not desirable for a relatively simple MRI procedure.

Certain NMR-based methods also exist that can minimize blurring of MRI images due to motion of the subject. One such method is called the navigator echo technique. The navigator echo technique is accomplished by acquiring a one-dimensional profile along the motion direction. This allows the respiratory phase to be measured at any given time. Once the respiratory phase has been determined, it can be used to produce artifact-free images, but this method is applicable only for simple motion that has a period that is long compared to the time required to acquire one phase-encoded step. Gradient moment nulling is another NMR based method for limiting or eliminating artifacts from motion. Gradient moment nulling eliminates the net evolution of nuclear spins moving in the magnetic field gradient by varying the amplitude and/or duration of the gradient. Gradient moment nulling, although applicable in human experiments, is an insufficient technique for small animal imaging.

There are also a number of direct non-NMR methods that are useful to eliminate blurring caused by motion. In particular, by detecting the respiratory motion of the subject, a gate signal can be generated that can be used in the collection and analysis of data from the MRI system by focusing only on the data collected while the subject's body is nearly motionless. Optical sensors can detect chest motion when placed on the chest of the subject. Motion can be detected for example by placing the fiber so that the motion causes the fiber to flex which interrupts the light propagation through the fiber. Optical fibers can also detect motion when the motion causes a variation in the distance of the chest to an infrared emitter/detector. Both methods of using optical fibers detect respiratory motion through monitoring of the absolute chest position. Such techniques are advantageous in that they do not require electrical leads inside the probe or magnet, but are limited because of the need for very careful placement and maintenance of the fiber on or near a specific part of the subject's chest. Another method of direct non-NMR detection of respiratory motion is through the use of a pickup coil. Pickup coils generate a signal through electromagnetic induction in a wire loop placed on the subject's chest within a magnetic field. In particular, as shown in FIG. 1, a wire 16 is looped around the abdomen of a subject 10 (here a mouse used for research) positioned on a patient handling bed (not shown) in a magnetic bore 12 of an MRI machine to form a pickup coil 18. The free ends of wire 16 are connected to a voltage measuring device 20 that is positioned outside of magnetic bore 12. When a magnetic field B 14 is applied by the MRI machine, the output from voltage measuring device 20 will provide a measure of the respiration of subject 10 when pickup coil 18 is positioned orthogonally to the direction of the magnetic field. Pickup coils are inexpensive to build and easy to use, but in some cases require wire leads to be placed within the radio frequency ("RF") coil and gradients. Prior art systems using pickup coils had leads that introduced RF interference artifacts, posed a potential hazard of burns due to mutual inductance within the RF and/or gradients, and were subject to artifacts in the respiratory signal during scanning.

There are also indirect non-NMR based methods that can be used to minimize artifacts caused by motion. Many of these methods are based on the effects (on the subject and the immediate area surrounding the subject) of breathing. One such method utilizes a pressure detector on the chest of the subject with a pressure sensor outside the RF coil. Examples of such detectors are strain gauges, air bellows, or balloons. Although the theory behind these types of sensors is straightforward, they are quite sensitive to temperature variations, drifting baselines, and leakage. Also, they are generally not amenable to use on small animals. For example, a decrease in the heart rate of a mouse of up to 30% has been observed when using a pressurized pillow against its abdomen to detect respiration, which change is undesirable when using mice to conduct genetic or drug testing. The temperature and carbon dioxide content of exhaled air can also be used to monitor respiration, but the response is too slow for use in small, rapidly breathing animals. Another method that takes advantage of the effects of respiration is plethysmography. A plethysmograph utilizes an airtight chamber housing the subject, and uses a remote airflow sensor to detect motion of the subject. Although this type of sensor is quite useful in animals, it is quite expensive, complex and limits access to the animal. It is also highly unlikely, because of the sealed chamber, that such a method would be used with human subjects. Photoplethysmography, can also be used. Photoplethysmography detects respiratory and cardiac variations in superficial blood flow by infrared light scattering, but is again not amenable to imaging of small animals.

There are also methods that use certain characteristics of the MRI imaging process itself. For example, respiratory ordered phase encoding (ROPE) which is generally used along with a technique (either NMR or non-NMR based) to measure respiratory motion, can be used to generate artifact-free images, but requires specialized hardware and software, not generally available on animal imaging systems, to reconstruct the data. The data is acquired and processed with a mathematical algorithm that uses the respiratory phase signal to correct for the simple motion caused by respiration. Another method is the measurement of probe Q modulation, which allows for the detection of both respiratory and cardiac motion but requires special spectrometer hardware and can be prone to errors due to non-respiratory motion of the animal.

A number of patents have been directed towards methods of reducing image blurring due to motion. For example, U.S. Pat. No. 5,035,244 (Stokar), basically discloses an improvement on ROPE. It is a method that measures respiratory displacement data and uses that data to set the phase encoding gradient in order to minimize artifacts caused by motion. The important aspect of the invention is the mathematical algorithm that is utilized to select the phase encoded gradient strengths based on the respiratory displacement data. The disadvantages of this method are first, that a standard sensor, which has significant drawbacks, is necessary to obtain the respiratory displacement data, and second that it does not remedy the effects of cardiac motion.

U.S. Pat. No. 5,038,785 (Blakely, et al.) discloses a method of using electrodes to monitor the cardiac cycle and an expansion belt to monitor the respiratory cycle of a subject being imaged. During a MRI scan, noise signals or spikes are superimposed on the cardiac cycle signal. A noise spike detector detects spikes. Specifically, a comparator compares each signal received from the electrodes with properties of a cardiac signal, such as the slope. When the comparator determines that a noise signal is being received, it gates a track and hold circuit. The track and hold circuit passes the received signal except when gated by the comparator. When gated by the comparator, the track and hold circuit continues to supply the same output amplitude as in the beginning of the gating period. A filter then smoothes the plateaus in the cardiac signal formed as the noise signal signals are removed.

U.S. Pat. No. 5,427,101 (Sachs, et al.) discloses a method of reducing motion artifacts in MRI images through use of an algorithm. The method first acquires an initial set of data frames that includes a mechanism for indicating a relative position of each frame. The positional markers in these data frames are then evaluated and those that are deemed positionally worse are reacquired.

U.S. Pat. No. 5,729,140 (Kruger, et al.) teaches to a method for removing artifacts from NMR images by acquiring two data sets from which a desired image can be reconstructed, calculating the correlation between the two data sets to produce a correlation array, and producing a corrected image from the correlation array.

U.S. Pat. No. 6,073,041 (Hu, et al.) discloses a method for the removal of signal fluctuation due to physiological factors such as respiration and cardiac pulsations. The technique comprises simultaneous measurement of physiological motion during MRI data acquisition. Then in post processing steps, imaging data are retrospectively ordered into unit physiological cycles, after which the physiological effects are estimated and removed from the MRI data.

U.S. Pat. No. 6,088,611 (Lauterbur, et al.) teaches to a method for obtaining high-resolution snapshot images of moving objects in MRI applications through the elimination of ghosting and other image artifacts. The method works by estimating motion frequency data, estimating the amplitude data for the motion frequency data, interpolating the motion frequency data and the amplitude data to generate snap-shot data frames, and generating snapshot images of each snapshot data frame.

U.S. Patent Publication No. US 2001/0183611 A1 (Fishbein, et al.) discloses a method for measuring the respiration of a subject that uses a small electromagnetic pickup coil coupled to a mechanical lever to sense the respiratory and cardiac motion of a subject in a MRI scanner. It generates an electrical signal that is proportional to the velocity of motion which can be used to synchronize the MRI scanner to prevent blurring induced by motion during the MRI scan. The apparatus uses a complex mechanical linkage to couple the pickup coil to the subject.

Commercially available sensors, as well as the methods and systems discussed above, are either unreliable, unworkable in certain situations, or are too expensive. Therefore, there remains a need for a method of detecting respiratory motion that is reliable, amenable to different kinds of subjects and inexpensive.

SUMMARY OF THE INVENTION

In a first embodiment, the present invention is an apparatus and method for measuring movement of a portion of the body of a subject in a magnetic field, comprising a cradle attached around the portion of the body of a subject; a length of wire having a first end and a second end, the length of wire forming a loop in a central portion thereof, the loop connected around the cradle and thereby encircling the portion of the body of the subject; and a voltage measuring device having a first input connected to the first end of the wire, a second input connected to the second end of the wire, and an output representing the respiration of the subject. In a further embodiment, the cradle is formed from a thin polycarbonate plastic strip and the length of wire is formed from a high resistance lead.

In a second embodiment, the present invention is an apparatus and method for measuring movement of a portion of the body of a subject and an electrocardiogram of the subject in a magnetic field, comprising a first ECG electrode attached to the subject; a first ECG lead having a first end connected to the first ECG electrode and a second end; a second ECG electrode attached to the subject; a second ECG lead having a first end connected to the second ECG electrode and a second end, the second ECG lead forming a loop in a central portion thereof, the loop connected around the portion of the body of the subject; and a voltage measuring device having a first input connected to the second end of the first ECG lead, a second input connected to the second end of the second ECG lead and an output representing the movement of the portion of the body of the subject and the electrocardiogram of the subject. Preferably, the second embodiment may further comprise a cradle attached around the portion of the body of the subject between the loop formed by the second ECG lead and the portion of the body of the subject. Preferably, as in the first embodiment, the cradle is formed from a thin polycarbonate plastic strip. Further, the ECG leads are preferably formed from high resistance leads.

In both embodiments, the voltage measuring device preferably comprises a Faraday shield; two RF filters mounted in the Faraday shield, each of the RF filters having an input and an output, the inputs of the RF filters forming the first input and the second input of the voltage measuring device, respectively; a differential amplifier having two inputs and an output, each of the inputs connected to a respective output of one of the two RF filters; a gradient filter having an input and an output, the input of the gradient filter connected to the output of the differential amplifier, and means for transmitting an output signal having an input connected to the output of the gradient filter and an output.

BRIEF DESCRIPTION OF THE DRAWINGS

These and other objects and advantages of the invention, as well as the details of the illustrative embodiments, will be more fully understood by reference to the following portion of the specification, taken in conjunction with the accompanying drawings, in which.

DETAILED DESCRIPTION OF THE PREFERRED EMBODIMENTS

Figure 1:
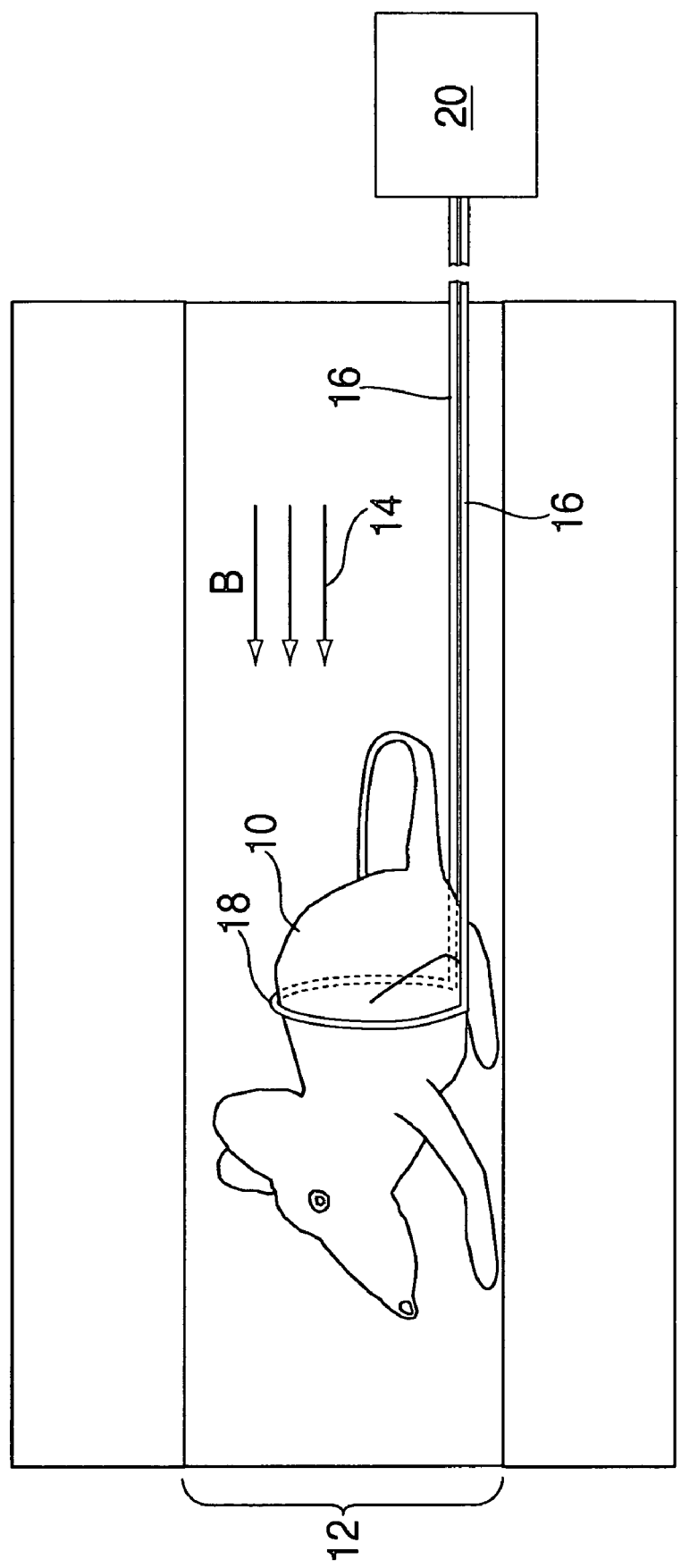
FIG. 1 illustrates the prior art use of a pickup coil.
Figure 2:
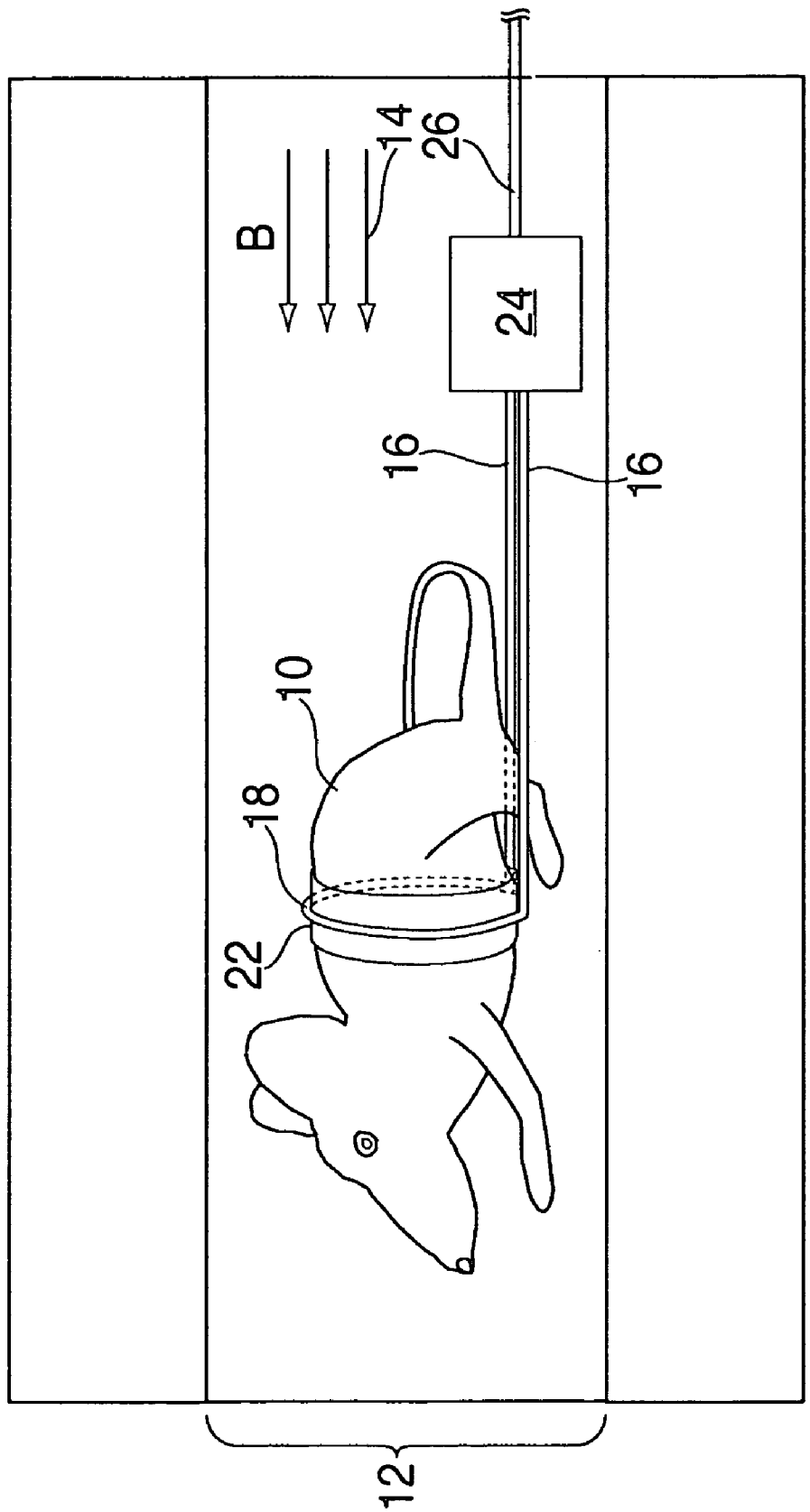
FIG. 2 illustrates one aspect of an apparatus in accordance with the invention.

Referring now to the drawing, and in particular FIG. 2 thereof, therein illustrated is a first embodiment of the present invention where, like the prior art system of FIG. 1, wire 16 is looped around the abdomen of subject 10 in magnetic bore 12 of an MRI machine to form pickup coil 18 for the measurement of the respiratory motion of subject 10. Here, however, wire 16 is formed from high resistance leads and the free ends thereof are connected to a voltage measuring device 24 that is positioned within magnetic bore 12. As discussed in greater detail with respect to FIG. 4, voltage measuring device 24 detects the voltage generated by pickup coil 18 when magnetic field B 14 is applied by the MRI machine and, preferably, converts that voltage to an optical signal for transmission through a fiber optic cable 26 to equipment outside the magnetic bore for further processing. As one of skill in the art will readily recognize, other types of signals may be used to transmit the signal from voltage measuring device 24. To improve the coupling of pickup coil 18 to the abdomen of subject 10, a cradle 22 is first positioned around subject 10, and pickup coil 18 is positioned around cradle 22. Cradle 22 is preferably made by thermoforming thin (i.e., approximately 0.010" thick) polycarbonate plastic strips in a cylindrical shape to conform to the abdomen of subject 10. Pickup coil 18 can be attached to cradle 22 by any number of means including, but not limited to, plastic tape. Cradle 22 and pickup coil 18 can be opened and placed around the abdomen of subject 10. The spring tension of cradle 22 should be light enough to not impede abdominal motion of subject 10, but strong enough for cradle 22 to open and close with the abdomen as the subject breathes. Cradle 22 can be made in various sizes to accommodate mammals of different sizes.

Figure 3:
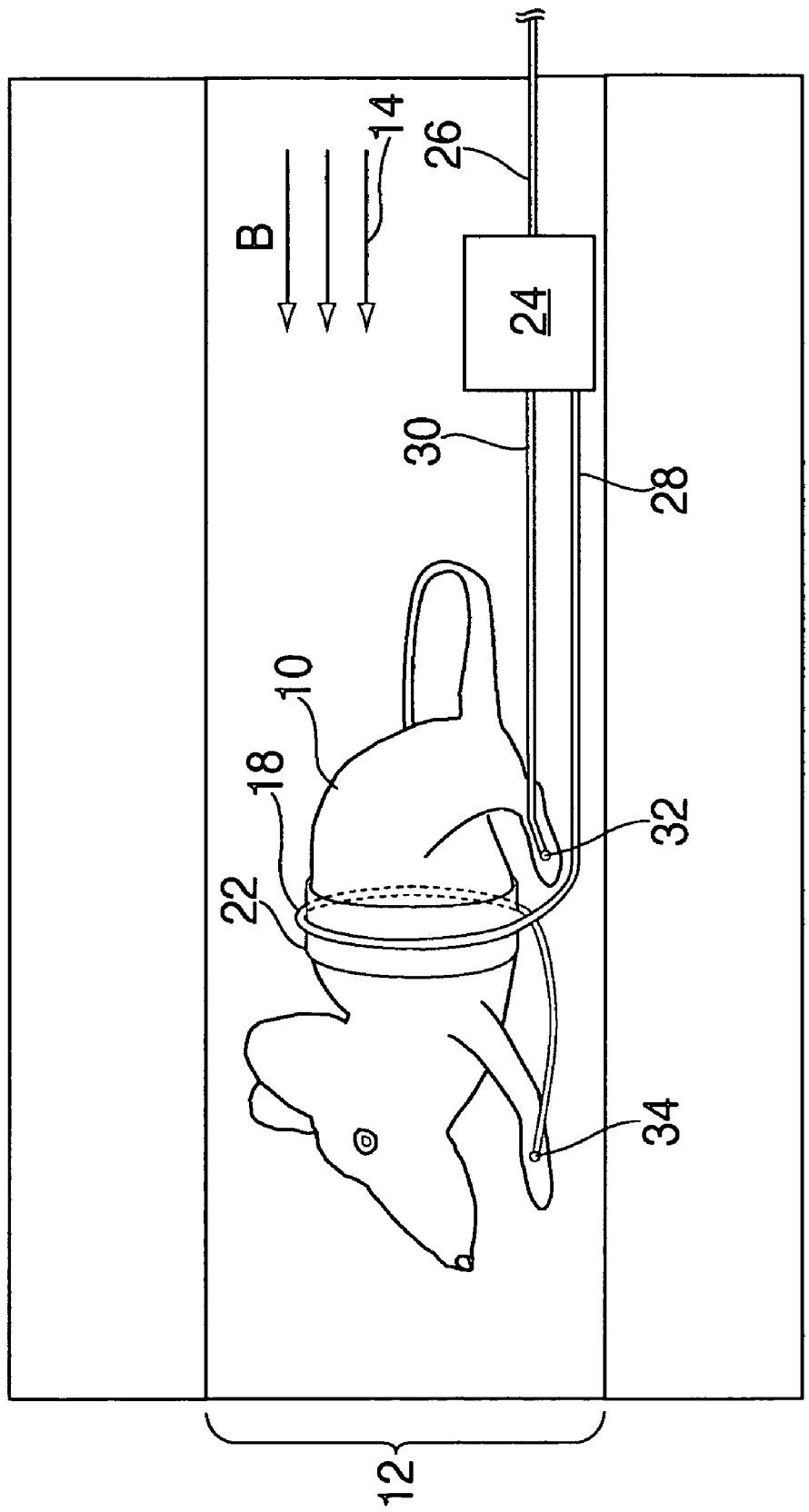
FIG. 3 illustrates another aspect of an apparatus in accordance with the invention.

Referring now to FIG. 3, a second embodiment of the present invention is illustrated, where the loop formed by wire 16 of FIG. 2 is replaced by two ECG lead wires 28 and 30 and the tissue of subject 10. In particular, subject 10 is shown within the magnetic bore 12 of an MRI machine. Two conventional ECG electrodes 32 and 34 are connected in a conventional manner to the body of subject 10. A first ECG lead wire 30 is connected between ECG electrode 32 and a first connection to voltage measuring device 24. A second ECG lead wire 28 is connected between ECG electrode 34 and a second connection to voltage measuring device 24 and a portion thereof is used to form pickup coil 18 around the abdomen of subject 10. Cradle 22 may be optionally used between pickup coil 18, formed by a portion of ECG lead wire 28, and the body of subject 10 to improve the coupling of pickup coil 18 to the body of subject 10, as with the first embodiment. ECG electrodes 32 and 34 are conventional and, as one of ordinary skill will readily recognize, can be any one of several types presently available, including but not limited to such electrodes as subdermal EEG needle electrodes from Nicolet Biomedical or gold-plated surface electrodes from Grass-Telefactor. Lead wires 28 and 30 should be as short as possible and preferably twisted where practical between measuring device 24 and subject 10 and flexible along the length attached to cradle 18. The output signal from measuring device 24 is preferably transmitted away from magnet bore 12 by fiber optic cable to other equipment outside magnet bore 12 for further processing, but, as one of ordinary skill will readily recognize, the signal transmitted from voltage measuring device 24 inside magnet bore 12 to equipment outside of bore 12 can be done by various other techniques.

In operation, when a magnetic field B 14 is applied, the electrode leadwire arrangement in FIG. 3 results in a measured voltage waveform which consists of an electrocardiogram of subject 10 and a respiration signal of subject 10 superimposed upon the electrocardiogram. The respiration signal results from movement of pickup coil 18 in the presence of magnetic field B 14. The size of the superimposed respiration signal is proportional to the length of wire forming pickup coil 18 and the strength of the magnetic field. For a typical magnetic field strength of 4.7 T, the leadwire arrangement as shown in FIG. 3 will result in a respiration waveform on the order of approximately 0.5 mV.

It can be advantageous to extract the respiration signal from the measured waveform to allow ease in detecting the respiratory event for determining respiration rate and for the generation of a respiratory gate signal. In the presence of a strong magnetic field, the electrocardiogram waveform often has a contribution from blood flow and from pulsed gradients. In the case of a cardiac gated pulse sequence, the R-wave (i.e., the neurological signal causing the heart to beat)) can be detected and a gate signal can be sent to the MRI system to activate data collection and gradient activity, since the heart starts to beat and blood begins to flow about 3 ms after the occurrence of the R-wave. In this case, signal contributions to the ECG from gradients and from flowing blood are both synchronous with the R-wave. Blood flowing in a strong magnetic field will generate flow artifacts in the ECG which are synchronous with the R-wave. Similarly, the gradient activity started by the R-wave gate is synchronous with the R-wave. The signals synchronous with the R-wave can be removed by a number of means known to those of skill in the art. One method that can be used is an averaging algorithm that computes the average waveform following R detection for the last several R-waves, e.g., the last ten R-waves, and continuously subtracts the average from the superimposed wave to obtain the respiration signal.

As described above, pickup coil 18 generates an electrical voltage signal when subject 10 breathes, due to the expansion of the torso during respiration, since such movement is orthogonal to the direction of magnetic field B 14. The magnitude of the electrical signal produced by the pickup coil 18 is determined in part by the size and configuration of pickup coil 18. In the preferred embodiment, pickup coil 18 is made by winding a wire into a single loop. However, as one of ordinary skill will readily recognize, as more loops are added to pickup coil 18, the signal that will be produced will increase when magnetic field B 14 is applied. Theoretically, pickup coil 18 may be characterized by the radius r of the circular area of the loop. However, a spiral coil can also be characterized by its radius, r, without introducing substantial error. Pickup coil 28 can comprise any nonmagnetic conductive material. For example, copper, silver, aluminum or the like. Preferably, pickup coil 18 is formed from copper wire.

Figure 4:
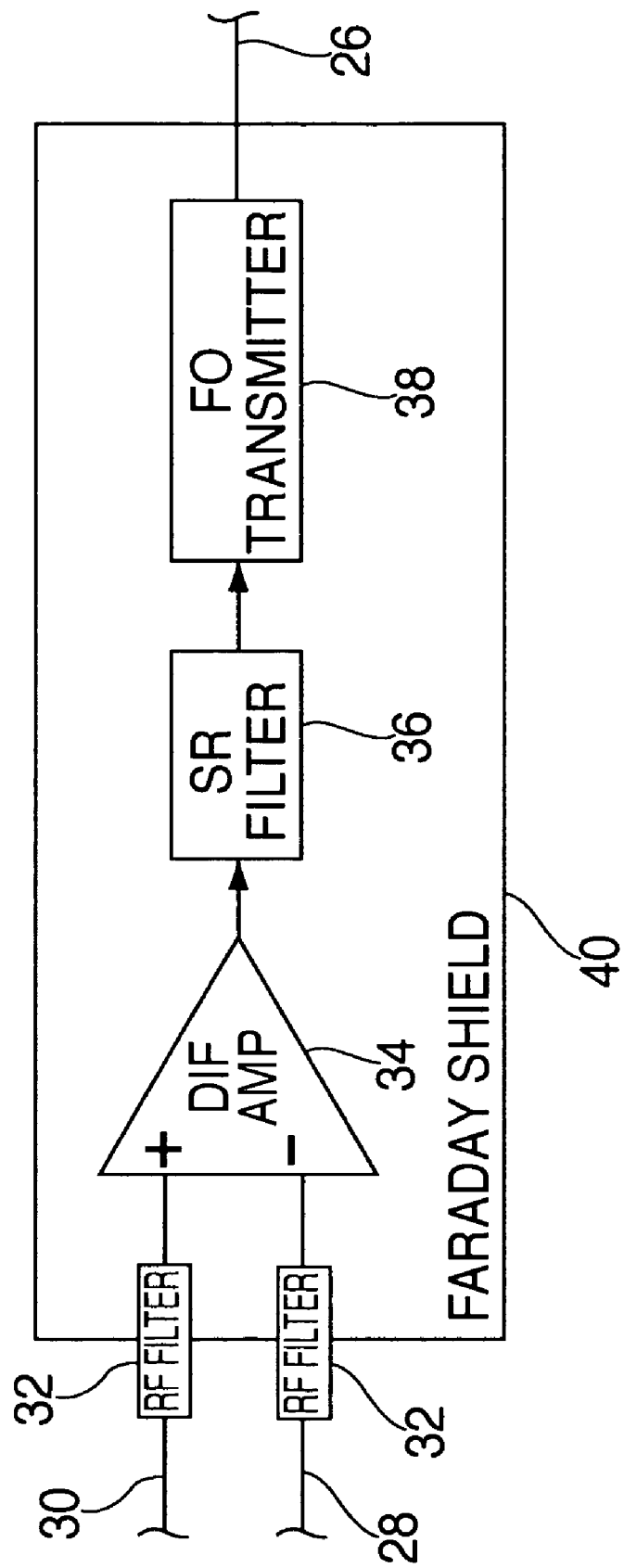
FIG. 4 is a schematic drawing of the invention.

Referring now to FIG. 4, two connections are provided by voltage measuring device 24 for lead wires 30 and 28 (or for each end of wire 16 of FIG. 2) through RF filters 32. Lead wires 30 and 28 are preferably short high resistance leads 50, with a preferred lead length of approximately 12" to minimize RF heating, to minimize induced spikes from switch gradients, to allow flexibility in electrode placement, and to allow voltage measuring device 24 to be optimally placed to avoid MRI image interference. Of course, as one of skill in the art will recognize, lead 28 must be longer than lead 30 to allow for the loop surrounding subject 10. Faraday shield 40 surrounds voltage measuring device 24 with RF filters 32 at the input port of Faraday shield 40. RF filters 32 and Faraday shield 40 prevent RF pulses, generated by the MRI tunnel and picked up by leads 28 and 30, from entering. RF filters 32 also prevent inference to the MRI signal from pulses generated in voltage measuring device 24. It is preferable for RF filters 32 to provide attenuation in excess of 50 dB at a frequency of 8.5 MHz and 70 dB at 85 MHz. One example of an RF filter for use with this invention would have a cutoff frequency of 16 kHz and an attenuation of 20 dB per decade of frequency. The use of Faraday shield 40 allows the placement of voltage measuring device 24 in close proximity of subject 10, allowing optimal positioning of voltage measuring device 24 and electrodes 32 and 34 separately thus reducing voltage and motion artifacts from affecting the ECG, respiration and MRI readings and preventing interference with the MRI imaging. Alternatively, a single RF filter 32 could be used, for example having its input connected to ECG lead 28, and the second ECG lead, e.g., ECG lead 30 could be connected directly to Faraday shield 40. In this case, one input of differential amplifier 34 would be connected to the output of single RF filter 32, and the second input of differential amplifier 34 would be connected to Faraday shield 40.

The output of RF filters 32 are input to a wide band (e.g. 0.1 Hz to 20 kHz), low gain differential amplifier 34. In the first embodiment, the output of amplifier 34 is an amplified version of the signal generated by pickup coil 18 which represents the respiration of subject 10. In the second embodiment, the output of amplifier 34 is an amplified version of ECG signals from leads 28 and 32 combined with a signal representing the respiration of subject 10. Optionally, the output of amplifier 34 could be supplied to a second amplifier, e.g., a wide band single ended amplifier, inserted prior to slew rate filter 36 if the gain of amplifier 34 proves to be less than optimal. The amplified signal, either the output of amplifier 34 or the optional wide band amplifier not shown, is applied to a gradient filter, e.g., slew rate filter 36, which suppresses voltage spikes from gradient pulses picked up by electrode leads 28 and 30. Preferably, a fast recovery slew rate filter is used which does not saturate with large induced spikes. It is preferable to set slew rate filter 36 to attenuate spikes with a slew rate greater than approximately 50 mv/msec. As one of ordinary skill will readily recognize, other types of gradient filters may be substituted for slew rate filter 32. The signal is then input to fiber optic transmitter 38 for conversion from an electrical signal to an optical signal.

The optical signal from fiber optic transmitter 38, modulated by the cardiac signal (second embodiment only) and the respiration signal (both embodiments), is transmitted from the voltage measuring device 24 and the MRI tunnel on fiber optic cable 26 to a fiber optic receiver for conversion back to an electrical signal. Both the cardiac portion of the received signal and the respiration portion of the received signal are then processed for display and the generation of gating signals, as understood by those of skill in the art.

The embodiments of the present invention have been shown for use in measuring the motion of the abdomen of a subject as a way to measure the respiration of the subject. However, as one of ordinary skill will readily recognize, the present invention has broad applications for the measurement of any kind of movement in a strong magnetic field. For example, eye movement can be detected if the pickup coil is coupled to the eyelid. Another example is specific muscle movement. If it is desired to track the movement of a particular muscle, the pickup coil can be looped around that muscle. Thus, so long as the pickup coil is looped around any portion of the body of the subject, movement of that portion of the body of the subject can be detected.

Although the present invention has been shown and described with respect to preferred embodiments, various changes and modifications which are obvious to a person skilled in the art of which the invention pertains are deemed to lie within the spirit and scope of the invention. Thus numerous changes and modifications can be made while staying within the scope of the invention which is set forth in the appended claims.

We claim:

1. An apparatus for producing a signal representing both the motion of an exterior portion of the body of a patient in a magnetic field and an electrocardiogram of the patient in the magnetic field, comprising:
    first and second ECG electrodes adapted to be attached to a patient positioned in said magnetic field;
    first and second ECG leads connected respectively to said first and second electrodes, said first ECG lead adapted to form a loop around at least part of said exterior portion of the body of said patient;
    a voltage measuring device having an input coupled to said ECG leads and producing an output signal having a first component induced by said magnetic field in the first ECG lead and representative of the motion of the exterior portion of the body of said patient and a second component representative of the electrocardiogram of said patient; and
    circuits responsive to said output signal for generating an ECG signal for display and a separate gating signal representative of the motion of the exterior portion of the body of said patient.

2. The apparatus of claim 1, further comprising a cradle adapted to be coupled around at least part of said portion of the body of said patient and coupled to said one of said ECG leads enclosing at least part of said portion of the body of said patient.

3. The apparatus of claim 2, wherein said cradle is formed from a thin polycarbonate plastic strip.

4. The apparatus of claim 1, wherein said ECG leads are formed from high resistance leads.

5. The apparatus of claim 1, wherein said voltage measuring device comprises:
    a Faraday shield forming an enclosure;
    two RF filters mounted in said Faraday shield, each of said RF filters having an input coupled to a respective one of said ECG leads and an output;
    a differential amplifier mounted within said enclosure and having two inputs and an output, each of said inputs coupled to a respective output of one of said two RF filters;
    a gradient filter mounted within said enclosure and having an input and an output, said input of said gradient filter coupled to said output of said differential amplifier, and a transmitter mounted within said enclosure and having an input coupled to said output of said gradient filter and an output representative of the motion of said portion of the body of said patient.

6. The apparatus of claim 1, wherein said voltage measuring device comprises:
    a Faraday shield forming an enclosure and coupled to a first one of said ECG leads;
    an RF filter mounted in said Faraday shield having an input coupled to a second one of said ECG leads and an output;
    a differential amplifier mounted within said enclosure and having two inputs and an output, one of said inputs coupled to said output of said RF filter and the other of said inputs connected to said Faraday shield;
    a gradient filter mounted within said enclosure and having an input and an output, said input of said gradient filter coupled to said output of said differential amplifier, and
    a transmitter mounted within said enclosure and having an input coupled to said output of said gradient filter and an output representative of the motion of said portion of the body of said patient.

7. A method of producing a signal representative of the motion of a portion of the body of a patient in a magnetic field and an electrocardiogram of the patient in the magnetic field, comprising:
    attaching first and second ECG electrodes and ECG leads to the patient;
    positioning at least one ECG lead to form a loop around at least part of said exterior portion of the body of the patient;
    producing an output signal having a first component induced by said magnetic field in said at least one ECG lead and representative of the motion of the exterior portion of the body of the patient and a second component representative of the electrocardiogram of the patient;
    generating an ECG signal for display from said output signal; and
    generating a gating signal representative of the motion of the exterior portion of the body of the patient from said output signal.

8. The method of claim 7, further comprising the step of positioning a cradle attached around at least part of the portion of the body of the patient, said cradle coupled to said second ECG lead.

9. The method of claim 8, wherein said cradle is formed from a thin polycarbonate plastic strip.

10. The method of claim 7, wherein said first ECG lead and said second ECG lead are formed from high resistance leads.

11. An apparatus for measuring motion of an exterior portion of the body of a patient in a magnetic field, comprising:
    means for detecting motion of the exterior portion of the body of said patient in the presence of said magnetic field;
    a voltage measuring device connected to said detecting means and having an output signal induced by the interaction of the motion of the exterior portion of the body of the patient and said magnetic field and representative of the motion of the exterior portion of the body of the patient; and
    means responsive to said output signal for generating a gating signal representative of the motion of the exterior portion of the body of said patient,
    said means for detecting motion of the exterior portion of the body of the patient comprising first and second ECG electrodes adapted for attachment to the patient and first and second ECG leads connected respectively to said first aid second electrodes, one of said ECG leads adapted for forming a loop around at least part of the exterior portion of the body of the patient.

12. An apparatus for measuring respiration of a patient positioned in a magnetic field, comprising:
    first and second ECG electrodes adapted to be attached to the patient positioned in a magnetic field;
    first and second ECG leads adapted to be connected respectively to said first and second electrodes, at least one of said ECG leads forming a loop around at least part of the exterior portion of the body of the patient;
    a voltage measuring device connected to first and second ECG leads and having an output signal having a first component induced by the motion of said at least one ECG lead in said magnetic field and representative of the respiration of the patient and a second component representative of the electrocardiogram of the patient;
    means for generating an ECG signal for display from said output signal from said voltage measuring device; and
    means for generating a gating signal representative of the respiration of said patient from said output signal from said voltage measuring device.

* * * * *